United States Patent [19]

Sulkowski et al.

[11] 4,321,384

[45] Mar. 23, 1982

[54] ANTIHYPERTENSIVE AGENTS

[75] Inventors: Theodore S. Sulkowski, Wayne; James L. Bergey, Lansdale; Albert A. Mascitti, Norristown, all of Pa.

[73] Assignee: American Home Products Corporation, New York, N.Y.

[21] Appl. No.: 238,911

[22] Filed: Feb. 27, 1981

[51] Int. Cl.$^3$ .............................. C07D 471/02
[52] U.S. Cl. ..................... 546/123; 544/362; 424/256; 424/250
[58] Field of Search ............ 546/123; 544/362; 424/256, 250

[56] References Cited

U.S. PATENT DOCUMENTS

| 3,325,505 | 6/1967 | Loev | 260/295.5 |
|---|---|---|---|
| 3,429,887 | 2/1969 | Lesher | 260/294.9 |
| 3,441,648 | 4/1969 | Loev et al. | 424/263 |
| 3,506,668 | 4/1970 | Lesher | 546/123 |
| 3,590,036 | 6/1971 | Lesher et al. | 546/123 |
| 3,600,394 | 8/1971 | Coyne et al. | 544/362 |
| 3,673,193 | 6/1972 | Lesher et al. | 546/123 |
| 3,773,773 | 11/1973 | Bossert | 260/294.8 |
| 3,799,934 | 3/1974 | Meyer et al. | 260/294.8 |
| 3,963,736 | 6/1976 | Nakagome et al. | 546/123 |
| 4,022,898 | 5/1977 | Meyer et al. | 424/251 |
| 4,038,399 | 7/1977 | Bossert et al. | 424/266 |
| 4,177,278 | 12/1979 | Bossert et al. | 424/266 |

FOREIGN PATENT DOCUMENTS 843576 of 0000 Belgium .

OTHER PUBLICATIONS

J. Med. Chem. 17, No. 9, 956 (1974).
Arzneim-Forsch 22, 22 (1972).
Arch. Pharmacol. 310, 69 (1979).
C.A.: 4823b.

Primary Examiner—Ethel G. Love
Attorney, Agent, or Firm—Richard K. Jackson

[57] ABSTRACT

1,4,5,6,7,8-hexahydro-2-alkyl-4-aryl-5-oxo-1,7-naphthyridine-3-carboxylic acid esters and pharmaceutically acceptable salts thereof are useful antihypertensive agents.

24 Claims, No Drawings

ANTIHYPERTENSIVE AGENTS

BACKGROUND OF THE INVENTION

Pharmacological agents possessing the ability to block cellular transmembrane influx of calcium are capable of suppressing that portion of myocardial or smooth muscle contractility which is dependent upon extracellular calcium. These pharmacological agents, termed calcium antagonists, have been proven to be useful in the treatment of hypertension, cardiac arrhythmias, angina pectoris, cardiac myopathy and coronary artery vasospasm (a possible cause of sudden cardiac death syndrome). Can J. Physiol. Pharmacol., 57 443 (1979); Drugs, 15 169 (1978); Acta Pharmacol. Toxicol., 43, suppl. 1, 45 (1978).

In theory, calcium antagonists are thought to act by blocking calcium influx through discrete calcium channels (slow channels) in cell membranes. Various tissues exhibit relative differences in sensitivity toward the calcium blocking effect achieved by certain calcium antagonists, theoretically as a result of tissue specific differences in the calcium channels. Acta Pharmacol. Toxicol., 43, 5, (1978); loc. cit. 291 (1978); Microvascular Res., 5 73 (1973); Am. Rev. Pharmacol. Toxicol., 17 149 (1977). Calcium channels of tissues which are most sensitive to calcium antagonist blockade are those which allow calcium influx only when the cell membranes are electrically depolarized. α-adrenergic receptor-activated calcium channels are relatively unaffected by these agents. Circ. Res., 46 426 (1980). This observation provides basis for evaluation of calcium antagonism.

Thus vascular smooth muscle tissue from the rabbit aorta can be made to contract when exposed to a depolarizing solution containing an elevated potassium ion concentration and normal amounts of calcium ions. Calcium antagonists added to the solution produce a dose dependent relaxation of the contracted rabbit aortic tissue. Normal contraction of the aortic tissue can then be induced in the presence of a calcium antagonist by subsequent addition of an α-adrenergic agonist, such as norepinephrine, to the solution. Eur. J. Pharmacol., 53 281 (1979); Circ. Res., 46 426 (1980); J. Exp. Pharmacol. Therap., 174 500 (1970). The normal contraction produced by an α-adrenergic agonist after maximal smooth muscle relaxation has been induced by a calcium antagonist, serves to distinguish the calcium blocking effect of an agent from a nonspecific depressant effect on the muscle.

DESCRIPTION OF THE INVENTION

In accordance with this invention there is provided a group of 1,4,5,6,7,8-hexahydro-2-alkyl-4-aryl-5-oxo-1,7-naphthyridine-3-carboxylic acid esters and pharmaceutically acceptable salts thereof, which compounds are calcium antagonists useful in the treatment of hypertension, cardiac arrhythmias, angina pectoris, cardiac myopathy and coronary artery vasospasm.

More specifically, the antihypertensive agents of this invention are compounds of the formula:

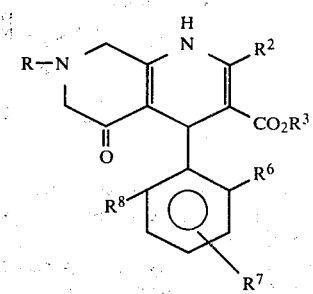

in which
R is hydrogen or alkyl of 1 to 6 carbon atoms;
$R^2$ is alkyl of 1 to 6 carbon atoms;
$R^3$ is alkyl of 1 to 6 carbon atoms, alkoxyalkyl in which each alkyl moiety has 1 to 6 carbon atoms, $-CH_2CF_3$, $-CH_2CH_2CF_3$ or

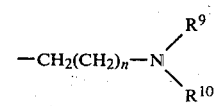

where
$R^9$ is hydrogen or alkyl of 1 to 6 carbon atoms; and
$R^{10}$ is alkyl of 1 to 6 carbon atoms or arylalkyl of 7 to 10 carbon atoms and $R^9$ and $R^{10}$ taken with the nitrogen atom to which they are attached form a pyrrolidinyl, imidazolidinyl, piperidyl, piperazinyl, 4-alkyl-piperazinyl in which the alkyl group contains from 1 to 6 carbon atoms or morpholinyl heterocycle; and
n is one of the integers 0, 1 or 2;
$R^6$ and $R^8$ are, independently, hydrogen, alkyl of 1 to 6 carbon atoms, halo, trifluoromethyl, alkoxy of 1 to 6 carbon atoms, alkylthio of 1 to 6 carbon atoms, cyano or nitro;
$R^7$ is hydrogen, alkyl of 1 to 6 carbon atoms, halo, trifluoromethyl, cyano or nitro; and
$R^6$ and $R^7$ when in ortho position to each other and taken together are butadienylene, tetramethylene or trimethylene;
or a pharmaceutically acceptable salt thereof.

With reference to the above described genus of compounds, the preferred variables, from the standpoint of production economics and availability of starting materials, are those in which the aliphatic moieties are straight or branched chain containing from 1 to 4 carbon atoms, the arylalkyl group representing $R^{10}$ is benzyl or phenethyl and n is 1 or 2.

The compounds of this invention are prepared by reaction of equimolar amounts 3-oxo-5-hydroxy-1,2,3,6-tetrahydropyridine derivatives (piperidine-3,5-diones), an aldehyde and a 3-aminocrotonate derivative, thusly:

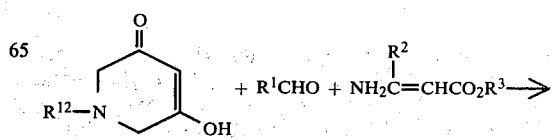

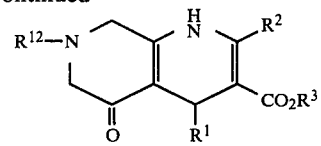

where $R^{12}$ is alkyl of 1 to 6 carbon atoms or benzyl. The benzyl group is removed by hydrogenolysis to afford the 7-unsubstituted products.

The aminoalkyl esters may be prepared by formation of the substituted aminocrotonate in situ via ammonolysis of the desired aminoalkyl acetoacetic acid ester.

The 3-oxo-5-hydroxy-1,2,3,6-tetrahydropyridines used as starting materials are prepared from N-substituted glycine esters by standard procedures. The N-methyl and N-benzyl 3-oxo-5-hydroxy-1,2,3,6-tetrahydropyridines are literature compounds. Archiv. der Pharmazie, 300 91 (1967); J.A.C.S. 95 7458 (1973); Tet. Lett., 4075 (1977). The preparatory technique generally follows the equations:

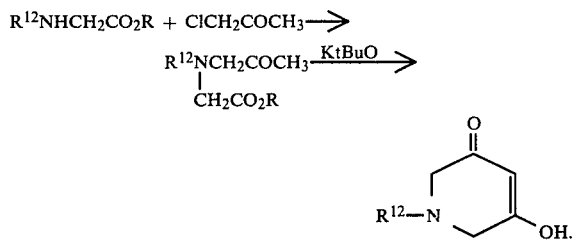

The aldehyde and amino crotonate reactants are either commercially available or may be prepared by standard procedures.

The pharmaceutically acceptable salts of the antihypertensive agents of this invention are prepared directly by neutralization of the free base or by metathetical displacement. The physiologically acceptable salts may be formed with organic or inorganic acids such as hydrochloric, hydrobromic, phosphoric, sulfuric, sulfonic, nitric, methylsulfonic, acetic, maleic, succinic, fumaric, tartaric, citric, salicylic, lactic, naphthalenesulfonic acid, and the like.

The N-benzyl 1,4,5,6,7,8-hexahydro-2-alkyl-4-aryl-5-oxo-1, 7-naphthyridine-3-carboxylic acid esters form an additional intermediate compound aspect of the invention useful in the preparation of the N-unsubstituted analogues referred to supra. The N-benzyl intermediates are depicted by the structural formula:

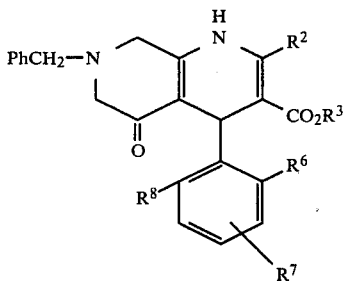

where $PhCH_2$ is benzyl and the $R^2$–$R^8$ groups are defined supra. These compounds, although categorized as intermediates herein, are very potent in vitro $Ca^{+2}$ antagonists generally lacking sufficient bioavailability in vivo (because of their insolubility, protein binding propensity or analogous functional deactivating property) to qualify as antihypertensive agents. Derivitization of the 7-benzyl intermediates to afford in vivo antihypertensive activity is achieved by functionalizing the compounds to provide solubility and avoid physical deactivation in the animal. Thus, the aminoalkyl esters illustrate one method for improving the bioavailability of the 7-benzyl derivatives such that they afford excellent antihypertensive agents without removal of the 7-benzyl substituent. The in vitro $Ca^{+2}$ antagonist activity level and the in vivo blood pressure reduction obtained, where applicable, for these intermediates, is presented in the following examples.

The compounds of this invention were initially shown to exhibit $Ca^{+2}$ antagonism in rabbit aortic strips wherein the strips were contracted in an organ bath containing a modified physiological salt solution (Broekaert et al., Europ. J. Pharmacol. 53 281 (1979)) in which 100 millimoles potassium ion had been substituted on an equimolar basis for sodium ion. After a stable active tension has developed in the strip, as measured by Statham UC-2 force transducers and recorded on an eight channel Beckman Dynograph Polygraphic Recorder, an amount of the antagonist was added to the organ bath to make a $10^{-5}$ molar concentration of antagonist. The depressent effect, expressed as percent relaxation, was taken from the mean of at least two experiments. After maximum $Ca^{+2}$ antagonist induced relaxation was obtained, a maximal dose of norepinephrine ($10^{-5}$ moles) was added to the organ bath to determine whether normal $\alpha$-adrenergic responses were still effected and show that the compound being tested was not a general depressant. A $Ca^{+2}$ antagonist producing a 20 percent relaxation of aortic tissue in this test procedure at a $10^{-5}$ molar bath concentration of the antagonist, generally produces a significant reduction in blood pressure when a sufficient amount is given to the spontaneously hypertensive rat.

The in vivo blood pressure lowering ability of the compounds of this invention was established by measuring the systolic pressure of spontaneously hypertensive rats with a Decker Caudal Plethysmograph or similar sensor device. The compound being tested is administered to groups of four rats and their blood pressure is read prior to compound administration and at 1.5 and 4 hours after compound administration. Depending upon the behavior of the compound being tested, the schedule of blood pressure readings and route of administration is modified. Initially the compounds are administered orally but where compound solubility is a factor, the compounds may be administered parenterally (i.e. i.p., i.m., s.c., i.v., etc.) as desired. The compounds of this invention were initially administered orally at a standard testing dose of 50 mg/kg.

Based upon the activity profile elicited by the compounds of this invention in the above-described standard scientifically recognized test models, the compounds are established as hypotensive agents useful in the treatment of hypertension and conditions characterized by constrictive blood flow in coronary arteries. For that purpose, the compounds may be administered orally or parenterally in suitable dosage forms compatable with the route of administration, whether oral, intraperitoneal, intramuscular, intravenous, intranasal, buccal, etc. The effective dose range determined in the animal test models has been established at from 1 to about 50 milligrams per kilogram host body weight to be administered in single or plural doses as needed to obtain the desired hypotensive response. The specific dosage regimen for a given patient will depend upon age, pathological state, severity of dysfunction, size of the patient, etc. Oral administration is performed with either a liquid or solid dosage unit in any conventional form such as tablets, capsules, solutions, etc., which comprise a unit dose (e.g. from about 25 milligrams to about 4 grams) of the active ingredient alone or in combination with adjuvants needed for conventional coating, tableting, solubilizing, flavor or coloring. Parenteral administration with liquid unit dosage forms may be via sterile solutions or suspensions in aqueous or oleagenous medium. Isotonic aqueous vehicle for injection is preferred with or without stabilizers, preservatives and emulsifiers.

The following examples illustrate the preparation of a representative number of compounds of this invention. After each example, the $Ca^{+2}$ antagonist activity of the compound is presented in terms of percent relaxation (P.R.) at the stated concentration. Similarly, the antihypertensive activity is reported in terms of millimeters mercury (mmHg) blood pressure (B.P.) reduction at the stated time post 50 mg/kg oral dosing.

EXAMPLE 1

1,4,5,6,7,8-Hexahydro-2,7-dimethyl-4-(2-nitrophenyl)-5-oxo-1,7-naphthyridine-3-carboxylic acid methyl ester 1-Methyl-3-oxo-5-hydroxy-1,2,3,6-tetrahydropyridine (6.36 g.), 5.93 g. of methyl-3-aminocrotonate (97%), 7.56 g. of o-nitrobenzaldehyde and 100 ml. of ethanol were heated at reflux for 1.5 hours. The mixture was cooled to room temperature and the precipitated solid was separated by filtration. The solid, m.p. 233°–235° C., was suspended in ethanol and saturated with hydrogen chloride. The solid dissolved, then reprecipitated. The mixture was cooled and the solid was separated by filtration. The solid was recrystallized from 90% ethanol with charcoal treatment to obtain the title compound as the hydrochloride, m.p. 227°–229° C. dec.

Analysis for: $C_{18}H_{19}N_3O_5 \cdot HCl$: Calculated: C, 54.90; H, 5.12; N, 10.67; Cl, 9.00. Found: C, 54.87; H, 5.20; N, 10.74; Cl, 8.96.

P.R.=14 at $10^{-5}$M

B.P.=−27 at 1.5 hours; −21 at 4 hours.

EXAMPLE 2

1,4,5,6,7,8-Hexahydro-2,7-dimethyl-4-(2-methylphenyl)-5-oxo-1,7-naphthyridine-3-carboxylic acid methyl ester A mixture of 7.65 g. of 1-methyl-3-oxo-5-hydroxy-1,2,3,6-tetrahydropyridine, 7.2 g. of o-tolualdehyde, 6.9 g. of methyl-3-aminocrotonate (97%), 110 ml. of ethanol and 35 ml. of acetic acid was refluxed for 3 hours. The mixture was evaporated to dryness in vacuo. The residue was dissolved in dichloromethane and extracted with saturated sodium carbonate solution. The dichloromethane solution was evaporated to dryness. The residue was slurried with diethyl ether and the solid was separated by filtration. Recrystallization from ethanol afforded the title compound, m.p. 249°–252° C. dec.

Analysis for: $C_{19}H_{22}N_2O_3$: Calculated: C, 69.91; H, 6.80; N, 8.58. Found: C, 70.07; H, 6.81; N, 8.73.

The solid was suspended in ethanol and saturated with hydrogen chloride. The solvent was removed in vacuo. The residue was recrystallized twice from ethanol-diethyl ether to obtain the hydrochloride, m.p. 245°–247° C. dec.

Analysis for: $C_{19}H_{22}N_2O_3 \cdot HCl$: Calculated: C, 62.89; H, 6.39; N, 7.72; Cl, 9.77. Found: C, 62.48; H, 6.36; N, 7.72; Cl, 9.75.

P.R.=31 at $10^{-5}$M

B.P.=−57 at 1.5 hours; −28 at 4 hours.

EXAMPLE 3

1,4,5,6,7,8-Hexahydro-2-methyl-4-(2-methylphenyl)-5-oxo-7-(phenylmethyl)-1,7-naphthyridine-3-carboxylic acid methyl ester A mixture of 6.1 g. of 1-benzyl-3-oxo-5-hydroxy-1,2,3,6-tetrahydropyridine, 3.6 g. of methyl-3-aminocrotonate (97%), 3.6 g. of o-tolualdehyde, 55 ml. of ethanol and 18 ml. of acetic acid was refluxed for 7 hours. The solution was evaporated to dryness in vacuo. The residue was triturated with diethyl ether and the solid was separated by filtration. Recrystallization from ethanol afforded the title compound, m.p. 201°–204° C.

Analysis for: $C_{25}H_{26}N_2O_3$: Calculated: C, 74.60; H, 6.51; N, 6.96. Found: C, 74.42; H, 6.57; N, 6.87.

P.R.=90 at $10^{-6}$M

B.P.=−23 at 1.5 hours; −41 at 4 hours.

EXAMPLE 4

1,4,5,6,7,8-Hexahydro-2,7-dimethyl-5-oxo-4-[2-(trifluoromethyl)-phenyl]-1,7-naphthyridine-3-carboxylic acid methyl ester 1-Methyl-3-oxo-5-hydroxy-1,2,3,6-tetrahydropyridine (6.36 g.), 5.93 g. of methyl-3-aminocrotonate, 8.70 g. of o-trifluoromethylbenzaldehyde and 100 ml. of ethanol were refluxed for 2 hours. The reaction mixture was filtered and allowed to cool to room temperature. The solid was separated by filtration. The solid, m.p. 250°–252° C. dec., was suspended in ethanol and saturated with hydrogen chloride. The solution was evaporated to dryness in vacuo. The residue was slurried with diethyl ether and filtered. Recrystallization from ethanol-diethyl ether afforded the title compound as the hydrochloride, m.p. 234°–237° C. dec.

Analysis for: $C_{19}H_{19}N_2F_3O_3 \cdot HCl$: Calculated: C, 54.74; H, 4.84; N, 6.72; Cl, 8.50. Found: C, 54.42; H, 4.90; N, 6.64; Cl, 8.46.

P.R.=48 at $10^{-5}$M

B.P.=−68 at 1.5 hours; −70 at 4 hours.

EXAMPLE 5

1,4,5,6,7,8-Hexahydro-2-methyl-5-oxo-7-(phenylmethyl)-4-[2-(trifluoromethyl)phenyl]-1,7-naphthyridine-3-carboxylic acid methyl ester A mixture of 8.5 g. of 1-benzyl-3-oxo-5-hydroxy-1,2,3,6-tetrahydropyridine, 4.75 g. of methyl-3-aminocrotonate (97%), 6.96 g. of o-trifluoromethylbenzaldehyde and 125 ml. of ethanol was refluxed for 2 hours. The mixture was filtered while hot and the filtrate was allowed to cool to room temperature. The solid was separated by filtration. Recrystallization from ethanol afforded the title compound, m.p. 225°–227° C.

Analysis for: $C_{25}H_{23}N_2F_3O_3$: Calculated: C, 65.78; H, 5.08; N, 6.14. Found: C, 65.68; H, 5.18; N, 6.04.

P.R.=40 at $10^{-6}$M

EXAMPLE 6

1,4,5,6,7,8-Hexahydro-2,7-dimethyl-4-(3-nitrophenyl)-5-oxo-1,7-naphthyridine-3-carboxylic acid methyl ester 1-methyl-3-oxo-5-hydroxy-1,2,3,6-tetrahydropyridine (5.10 g.), 4.75 g. of methyl-3-aminocrotonate (97%), 6.05 g. of m-nitrobenzaldehyde and 100 ml. of ethanol were refluxed for 1.5 hours. The mixture was filtered while hot and allowed to cool to room temperature. The solid was separated by filtration. The solid, m.p. 210° C. dec., was suspended in ethanol and saturated with hydrogen chloride. The solution was filtered and evaporated to dryness. The residue was slurried with diethyl ether and filtered. Two recrystallizations from ethanol afforded the title compound as the hydrochloride, m.p. 220° C. dec.

Analysis for: $C_{18}H_{19}N_3O_5 \cdot HCl$: Calculated: C, 54.90; H, 5.12; N, 10.67; Cl, 9.00. Found: C, 54.89; H, 5.19; N, 10.76; Cl, 8.95.

P.R.=35 at $10^{-5}M$

B.P.=−85 at 1.5 hours; −47 at 4 hours.

EXAMPLE 7

1,4,5,6,7,8-Hexahydro-2-methyl-4-(2-methylphenyl)-5-oxo-1,7-naphthyridine-3-carboxylic acid methyl ester Twelve grams of 1,4,5,6,7,8-hexahydro-2-methyl-4-(2-methylphenyl)-5-oxo-7-(phenylmethyl)-1,7-naphthyridine-3-carboxylic acid methyl ester (Example 3) were suspended in 150 ml. of 95% ethanol and 2.5 ml. of concentrated hydrochloric acid. One-half gram of 10% palladium on carbon was added and the mixture was shaken with hydrogen at an initial pressure of 50 psi. After 7.5 hours, the mixture was filtered to remove the catalyst. The filtrate was evaporated to dryness in vacuo. The residue was slurried with ethanol and filtered. Recrystallization from 95% ethanol afforded the title compound as the hydrochloride, m.p. 278°–280° C. dec.

Analysis for: $C_{18}H_{20}N_2O_3 \cdot HCl$: Calculated: C, 61.97; H, 6.07; N, 8.03; Cl, 10.18. Found: C, 62.02; H, 6.19; N, 8.23; Cl, 9.96.

P.R.=46 at $10^{-5}M$

B.P.=−77 at 1.5 hours; −64 at 4 hours.

EXAMPLE 8

4-(2-chlorophenyl)-1,4,5,6,7,8-Hexahydro-2,7-dimethyl-5-oxo-1,7-naphthyridine-3-carboxylic acid methyl ester 1-Methyl-3-oxo-5-hydroxy-1,2,3,6-tetrahydropyridine (5.10 g.), 4.75 g. of methyl-3-aminocrotonate, 5.62 g. of o-chlorobenzaldehyde and 85 ml. of ethanol were heated to reflux. Solid began to precipitate after 15 minutes. Refluxing was continued for 45 minutes. The mixture was cooled and the solid was separated by filtration. The solid, m.p. 253°–255° C. dec, was suspended in ethanol and saturated with hydrogen chloride. The solution was evaporated in vacuo. The residue was slurried with diethyl ether and filtered. Two recrystallizations from ethanol-diethyl ether afforded the title compound as the hydrochloride, m.p. 241°–243° C. dec.

Analysis for: $C_{18}H_{19}N_2ClO_3 \cdot HCl$: Calculated: C, 56.40; H, 5.26; N, 7.31; Cl, 18.46. Found: C, 56.21; H, 5.30; N, 7.19; Cl, 18.17.

P.R.=28.3 at $10^{-5}M$

B.P.=−54 at 1.5 hours; −30 at 4 hours

EXAMPLE 9

4-(2,6-Dichlorophenyl)-1,4,5,6,7,8-hexahydro-2,7-dimethyl-5-oxo-1,7-naphthyridine-3-carboxylic acid methyl ester A mixture of 7.25 g. of 1-methyl-3-oxo-5-hydroxy-1,2,3,6-tetrahydropyridine, 8.75 g. of 2,6-dichlorobenzaldehyde, 5.94 g. of methyl-3-aminocrotonate (97%) and 135 ml. of ethanol were heated at reflux for 3 hours. The mixture was filtered and the filtrate was evaporated to dryness. The residue was slurried with ethanol and the solid was separated by filtration. The solid, m.p. 258°–260° C. dec, was suspended in ethanol and saturated with hydrogen chloride. The solution was evaporated to dryness. The residue was triturated with a small volume of ethanol and filtered. The solid was recrystallized from 95% ethanol to obtain the title compound as the hydrochloride, m.p. 260°–262° C. dec.

Analysis for: $C_{18}H_{18}Cl_2N_2O_3 \cdot HCl$: Calculated: C, 51.75; H, 4.58; N, 6.71; Cl, 25.66. Found: C, 51.71; H, 4.67; N, 7.06; Cl, 24.77.

P.R.=41.5 at $10^{-5}M$

B.P.=−22 at 1.5 hours; −43 at 4 hours.

EXAMPLE 10

1,4,5,6,7,8-Hexahydro-2-methyl-4-(3-nitrophenyl)-5-oxo-7-(phenylmethyl)-1,7-naphthyridine-3-carboxylic acid methyl ester 1-Benzyl-3-oxo-5-hydroxy-1,2,3,6-tetrahydropyridine (10.6 g.), 5.45 g. of methyl-3-aminocrotonate, 7.55 g. of m-nitrobenzaldehyde and 120 ml. of ethanol were heated at reflux for 3 hours. The mixture was filtered and the filtrate was cooled in an ice bath. The precipitated solid was separated by filtration. The solid, m.p. 189°–191° C. dec., was suspended in ethanol and saturated with hydrogen chloride. The salt was separated and recrystallized from aqueous ethanol to obtain the title compound as the hydrochloride, m.p. 211°–214° C. dec.

Analysis for: $C_{24}H_{23}N_3O_5 \cdot HCl$: Calculated: C, 61.34; H, 5.15; N, 8.94; Cl, 7.54. Found: C, 60.99; H, 5.32; N, 8.71; Cl, 7.56.

P.R.=89.7 at $10^{-6}M$

EXAMPLE 11

4-(2,5-Dimethylphenyl)-1,4,5,6,7,8-hexahydro-2,7-dimethyl-5-oxo-1,7-naphthyridine-3-carboxylic acid methyl ester A mixture of 5.10 g. of 1-methyl-3-oxo-5-hydroxy-1,2,3,6-tetrahydropyridine, 4.75 g. of methyl-3-aminocrotonate, 5.38 g. of 2,5-dimethylbenzaldehyde and 100 ml. of ethanol was refluxed for 1.5 hours. The mixture was filtered and allowed to cool to room temperature. The solid was separated by filtration. The solid, m.p. 270° C. dec, was suspended in ethanol and saturated with hydrogen chloride. The solution was evaporated to dryness in vacuo. The residue was recrystallized from 95% ethanol to obtain the title compound as the hydrochloride, m.p. 243°–246° C. dec.

Analysis for: $C_{20}H_{24}N_2O_3 \cdot HCl$: Calculated: C, 63.73; H, 6.68; N, 7.43; Cl, 9.41. Found: C, 63.52; H, 6.60; N, 7.46; Cl, 9.39.

P.R.=22 at $10^{-5}M$

EXAMPLE 12

1,4,5,6,7,8-Hexahydro-2-methyl-5-oxo-4-[2-(trifluoromethyl)phenyl]-1,7-naphthyridine-3-carboxylic acid methyl ester The hydrochloride prepared from 11.5 g. of 1,4,5,6,7,8-hexahydro-2-methyl-5-oxo-7-(phenylmethyl)-4-[2-(trifluoromethyl)-phenyl]-1,7-naphthyridine-3-carboxylic acid methyl ester (Example 5) was dissolved in 150 ml. of 90% methanol. One gram of 10% palladium on carbon was added and the mixture was shaken with hydrogen at an initial pressure of 50 psi. After 3 hours, the mixture was filtered to remove the catalyst. The filtrate was evaporated to dryness. The residue was slurried with diethyl ether and filtered. Recrystallization from methanol-diethyl ether afforded the title compound as the hydrochloride, m.p. 272°–275° C. dec.

Analysis for: $C_{18}H_{17}N_2F_3O_3 \cdot HCl$: Calculated: C, 53.67; H, 4.50; N, 6.95; Cl, 8.80. Found: C, 53.64; H, 4.54; N, 6.85; Cl, 8.74.

P.R.=89.1 at $10^{-5}M$
B.P.=$-88$ at 1.5 hours

EXAMPLE 13

1,4,5,6,7,8-Hexahydro-2-methyl-4-(3-nitrophenyl)-5-oxo-1,7-naphthyridine-3-carboxylic acid methyl ester 1,4,5,6,7,8-Hexahydro-2-methyl-4-(3-nitrophenyl)-5-oxo-7-(phenylmethyl)-1,7-naphthyridine-3-carboxylic acid methyl ester hydrochloride (8.5 g.) (Example 10) was dissolved in 250 ml. of 90% methanol. One-half gram of 10% palladium on carbon was added and the mixture was shaken with hydrogen at atmospheric pressure. Hydrogen uptake ceased after 45 minutes. The mixture was filtered to remove the catalyst and the filtrate was concentrated to dryness in vacuo. The residue was crystallized from isopropanol. Recrystallization from ethanol afforded the title compound as the hydrochloride, hemihydrate, m.p. 244° C. dec.

Analysis for: $C_{17}H_{17}N_3O_5 \cdot HCl \cdot \frac{1}{2}H_2O$: Calculated: C, 52.52; H, 4.92; N, 10.81; Cl, 9.12. Found: C, 52.46; H, 4.82; N, 11.06; Cl, 9.68.

P.R.=86.5 at $10^{-5}M$
B.P.=(Dose 25 mg/kg) $-58$ at 1.5 hours.

EXAMPLE 14

1,4,5,6,7,8-Hexahydro-2-methyl-5-oxo-4-[3-(trifluoromethyl)phenyl]-1,7-naphthyridine-3-carboxylic acid methyl ester A mixture of 10.5 g. of 1-benzyl-3-oxo-5-hydroxy-1,2,3,6-tetrahydropyridine, 5.95 g. of methyl-3-aminocrotonate (97%), 8.7 g. of 3-trifluoromethylbenzaldehyde and 120 ml. of ethanol was refluxed for 3 hours. The solution was concentrated to dryness. The residue was triturated with ethanol and the solid was separated by filtration. The solid was suspended in methanol and saturated with hydrogen chloride. The solid was separated and recrystallized from ethanol to obtain 1,4,5,6,7,8-hexahydro-2-methyl-5-oxo-7-(phenylmethyl)-4-[3-(trifluoromethyl)phenyl]-1,7-naphthyridine-3-carboxylic acid methyl ester hydrochloride, m.p. 225° C. dec.

Analysis for: $C_{25}H_{23}N_2F_3O_3 \cdot HCl$: Calculated: C, 60.92; H, 4.91; N, 5.68; Cl, 7.19. Found: C, 60.76; H, 5.07; N, 5.58; Cl, 7.52.

P.R.=46.2 at $10^{-6}M$

Nine grams of the above hydrochloride, 0.5 g. of 10% palladium on carbon and 250 ml. of methanol were shaken with hydrogen at an initial pressure of 40 psi. After 2 hours, the mixture was filtered to remove the catalyst. The filtrate was evaporated to dryness in vacuo and the residue crystallized on standing overnight. Recrystallization from ethyl acetate- diethyl ether afforded the title compound as the hydrochloride, m.p. 232°–234° C. dec.

Analysis for: $C_{18}H_{17}N_2F_3O_3 \cdot HCl$: Calculated: C, 53.67; H, 4.50; N, 6.95; Cl, 8.80. Found: C, 53.65; H, 4.67; N, 6.99; Cl, 8.83.

P.R.=84.0 at $10^{-5}M$
B.P.=$-51$ at 1.5 hours; $-43$ at 4 hours.

EXAMPLE 15

4-(2-Fluorophenyl)-1,4,5,6,7,8-hexahydro-2-methyl-5-oxo-1,7-naphthyridine-3-carboxylic acid methyl ester A mixture of 10.5 g. of 1-benzyl-3-oxo-5-hydroxy-1,2,3,6-tetrahydropyridine, 5.95 g. of methyl-3-aminocrotonate (97%) 6.2 g. of 2-fluorobenzaldehyde and 125 ml. of ethanol was refluxed for 3 hours. The precipitated solid was separated by filtration. The solid was suspended in methanol and saturated with hydrogen chloride. The solid was separated and recrystallized from 95% ethanol to obtain 4-(2-fluorophenyl)-1,4,5,6,7,8-hexahydro-2-methyl-5-oxo-7-(phenylmethyl)-1,7-naphthyridine-3-carboxylic acid methyl ester hydrochloride, m.p. 237° C. dec.

Analysis for: $C_{24}H_{23}N_2FO_3 \cdot HCl$: Calculated: C, 65.08; H, 5.46; N, 6.32; Cl, 8.00. Found: C, 64.97; H, 5.57; N, 6.31; Cl, 8.05.

P.R.=48 at $10^{-6}M$.

Ten grams of the above hydrochloride, 0.5 g. of 10% palladium on carbon, 200 ml. of methanol and 15 ml. of water were shaken with hydrogen at an initial pressure of 40 psi. After 2 hours, the catalyst was separated by filtration and the filtrate was evaporated to dryness in vacuo. The solid residue was slurried with acetonitrile, filtered, and dried in vacuo. Recrystallization from 95% ethanol afforded the title compound as the hydrochloride, m.p. 262°–263° C. dec.

Analysis for: $C_{17}H_{17}N_2FO_3 \cdot HCl$: Calculated: C, 57.88; H, 5.14; N, 7.94; Cl, 10.05. Found: C, 57.58; H, 5.15; N, 7.41; Cl, 10.05.

P.R.=54 at $10^{-5}M$
B.P.=$-45$ at 1.5 hours.

EXAMPLE 16

4-(3-Cyanophenyl)-1,4,5,6,7,8-Hexahydro-2,7-dimethyl-5-oxo-1,7-naphthyridine-3-carboxylic acid methyl ester 1-Methyl-3-oxo-5-hydroxy-1,2,3,6-tetrahydropyridine (6.6 g.) 5.95 g. of methyl-3-aminocrotonate (97%), 6.5 g. of 3-cyanobenzaldehyde and 125 ml. of ethanol were refluxed for 3 hours. The solvent was removed in vacuo and the residue was crystallized from a small volume of ethanol. The solid was suspended in methanol and saturated with hydrogen chloride. The solution was evaporated to dryness. The residue crystallized on standing in a small volume of ethanol. The solid was recrystallized from ethanol to obtain the title compound as the hydrochloride, m.p. 226°–229° C. dec.

Analysis for: $C_{19}H_{19}N_3O_3 \cdot HCl$: Calculated: C, 61.05; H, 5.39; N, 11.24; Cl, 9.48. Found: C, 60.09; H, 5.66; N, 11.16; Cl, 9.36.

P.R.=66 at $10^{-5}M$

B.P.=−53 at 1.5 hours

EXAMPLE 17

4-(2,3-Dimethylphenyl)-1,4,5,6,7,8-hexahydro-2,7-dimethyl-5-oxo-1,7-naphthyridine-3-carboxylic acid methyl ester 1-Methyl-3-oxo-5-hydroxy-1,2,3,6-tetrahydropyridine (6.36 g.), 5.93 g. of methyl-3-aminocrotonate (97%), 11 g. of 2,3-dimethylbenzaldehyde and 100 ml. of ethanol were refluxed for 3 hours. The mixture was filtered while hot and then left standing overnight. The precipitated solid was separated by filtration. The solid was suspended in methanol and saturated with hydrogen chloride. The solvent removed in vacuo. The residue was recrystallized from ethanol to obtain the title compound as the hydrochloride, m.p. 244°-247° C. dec.

Analysis for: $C_{20}H_{24}N_2O_3 \cdot HCl$: Calculated: C, 63.73; H, 6.68; N, 7.43; Cl, 9.41. Found: C, 63.85; H, 6.77; N, 7.38; Cl, 9.33.

P.R.=54 at $10^{-5}M$
B.P.=−40 at 4 hours.

EXAMPLE 18

4-[2-(n-butyl)phenyl]-1,4,5,6,7,8-Hexahydro-2-methyl-5-oxo-7-(phenylmethyl)-1,7-naphthyridine-3-carboxylic acid methyl ester A mixture of 10.6 g. of 1-benzyl-3-oxo-5-hydroxy-1,2,3,6-tetrahydropyridine, 5.95 g. of methyl-3-aminocrotonate (97%), 8.1 g. of 2-(n-butyl)benzaldehyde and 125 ml. of ethanol was refluxed for 3 hours. The solvent was removed in vacuo. The viscous residue was crystallized by dissolving in ethanol and cooling in an ice bath. The solid was dissolved in methanol and saturated with hydrogen chloride. The solution was evaporated to a solid residue. Recrystallization from 95% ethanol afforded the title compound as the hydrochloride, m.p. 220°-223° C. dec.

Analysis for: $C_{28}H_{32}N_2O_3 \cdot HCl$: Calculated: C, 69.91; H, 6.91; N, 5.82; Cl, 7.37. Found: C, 69.42; H, 7.09; N, 5.61; Cl, 7.42.

P.R.=61 at $10^{-6}M$.

EXAMPLE 19

4-[2-(n-butyl)phenyl]-1,4,5,6,7,8-hexahydro-2-methyl-5-oxo-1,7-naphthyridine-3-carboxylic acid methyl ester 4-[2-(n-butyl)phenyl]-1,4,5,6,7,8-hexahydro-2-methyl-5-oxo-7-(phenylmethyl)-1,7-naphthyridine-3-carboxylic acid methyl ester hydrochloride (9.5 g), 0.5 g. of 10% palladium on carbon, 200 ml. of methanol and 50 ml. of water were shaken with hydrogen at an initial pressure of 40 psi. After 2 hours, the catalyst was separated by filtration. The filtrate was evaporated in vacuo to a solid residue. Recrystallization from ethanol afforded the title compound as the hydrochloride, m.p. 259°-260° C.

Analysis for: $C_{21}H_{26}N_2O_3 \cdot HCl$: Calculated: C, 64.52; H, 6.96; N, 7.16; Cl, 9.07. Found: C, 64.41; H, 7.01; N, 7.31; Cl, 9.18.

P.R.=49.2 at $10^{-5}M$
B.P.=−24 at 1.5 hours.

EXAMPLE 20

4-(2,3-dimethylphenyl)-1,4,5,6,7,8-hexahydro-2-methyl-5-oxo-7-(phenylmethyl)-1,7-naphthyridine-3-carboxylic acid methyl ester A mixture of 16.2 g. of 1-benzyl-3-oxo-5-hydroxy-1,2,3,6-tetrahydropyridine, 9.2 g. of methyl-3-aminocrotonate, 11.6 g. of 2,3-dimethylbenzaldehyde and 180 ml. of ethanol was heated at reflux for 3 hours. The solvent was removed in vacuo and the residue was recrystallized from ethanol to obtain 14 g. of solid, m.p. 208°-211° C. The solid was suspended in methanol and saturated with hydrogen chloride. The solvent was removed in vacuo. The residue was recrystallized from methanol to obtain the title compound as the hydrochloride, m.p. 238°-239° C. d.

Analysis for: $C_{26}H_{28}N_2O_3 \cdot HCl$: Calculated: C, 68.94; H, 6.45; N, 6.18; Cl, 7.83. Found: C, 68.78; H, 6.51; N, 6.41; Cl, 7.77.

P.R.=33.3 at $10^{-6}M$; 80.4 at $10^{-5}M$
B.P.=−24 at 1.5 hours; −39 at 4 hours.

EXAMPLE 21

4-(2,3-dimethylphenyl)-1,4,5,6,7,8-hexahydro-2-methyl-5-oxo-1,7-naphthyridine-3carboxylic acid methyl ester Eight grams of the compound produced in Example 20, 0.5 g. of 10% palladium on carbon, 200 ml. of methanol, 50 ml. of water and 3 drops of concentrated hydrochloric acid were shaken with hydrogen at an initial pressure of 40 p.s.i. After two hours, the catalyst was separated by filtration. The filtrate was evaporated to dryness in vacuo. The residue was triturated with ethanol and separated to obtain the title compound as the hydrochloride, m.p. 254°-255° C., dec.

Analysis for: $C_{19}H_{22}N_2O_3 \cdot HCl$: Calculated: C, 62.89; H, 6.39; N, 7.72; Cl, 9.77. Found: C, 62.51; H, 6.58; N, 7.76; Cl, 9.46.

P.R.=76.7 at $10^{-5}M$
B.P.=−42 at 1.5 hours; −45 at 4 hours.

EXAMPLE 22

1,4,5,6,7,8-Hexahydro-2-methyl-5-oxo-7-phenylmethyl-4-[2-(trifluoromethyl)phenyl]-1,7-naphthyridine-3-carboxylic acid, 2-(N-benzyl-N-methylamino)ethyl ester A mixture of 15.2 g. of 1-benzyl-3-oxo-5-hydroxy-1,2,3,6-tetrahydropyridine, 13.1 g. of o-trifluoromethylbenzaldehyde, 18.7 g. of 2-(N-benzyl-N-methylamino)ethyl acetoacetate, 6 ml. of 28% ammonium hydroxide and 200 ml. of isopropanol was heated at reflux for 3 hours. The solution was evaporated to dryness. The residue was dissolved in 100 ml. of methylenechloride and extracted with 150 ml. of 15% hydrochloric acid. The acid extract was cooled and made basic with saturated sodium carbonate solution. The mixture was extracted with methylenechloride. The methylenechloride solution was dried over magnesium sulfate, then evaporated in vacuo to a solid residue. The residue was recrystallized from ethanol to obtain the title compound, m.p. 183°-185° C.

Analysis for: $C_{34}H_{34}N_3F_3O_3$: Calculated: C, 69.25; H, 5.81; N, 7.12. Found: C, 68.90; H, 6.02; N, 7.27.

P.R.=55.6 at $10^{-6}M$
B.P.=−74 at 1.5 hours; −68 at 4 hours.

What is claimed is:

1. A compound of the formula:

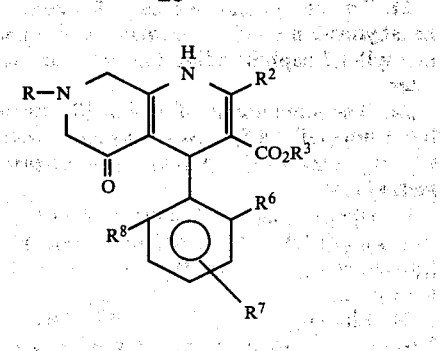

in which
R is hydrogen or alkyl of 1 to 6 carbon atoms;
R² is alkyl of 1 to 6 carbon atoms;
R³ is alkyl of 1 to 6 carbon atoms, alkoxyalkyl in which each alkyl moiety has 1 to 6 carbon atoms, —CH₂CF₃, —CH₂CH₂CF₃ or

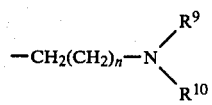

where R⁹ is hydrogen or alkyl of 1 to 6 carbon atoms and R¹⁰ is alkyl of 1 to 6 carbon atoms or arylalkyl of 7 to 10 carbon atoms and R⁹ and R¹⁰ taken with the nitrogen atom to which they are attached form a pyrrolidinyl, imidazolidinyl, piperidyl, piperazinyl, 4-alkylpiperazinyl in which the alkyl group contains from 1 to 6 carbon atoms or morpholinyl heterocycle, and n is one of the integers 0, 1 or 2;
R⁶ and R⁸ are, independently, hydrogen, alkyl of 1 to 6 carbon atoms, halo, trifluoromethyl, alkoxy of 1 to 6 carbon atoms, alkylthio of 1 to 6 carbon atoms, cyano or nitro;
R⁷ is hydrogen, alkyl of 1 to 6 carbon atoms, halo, trifluoromethyl, cyano or nitro;
and
R⁶ and R⁷ when in ortho position to each other and taken together are butadienylene, tetramethylene or trimethylene;
or a pharmaceutically acceptable salt thereof.

2. The compound of claim 1 which is 1,4,5,6,7,8-hexahydro-2,7-dimethyl-4-(2-nitrophenyl)-5-oxo-1,7-naphthyridine-3-carboxylic acid methyl ester.

3. The compound of claim 1 in which is 1,4,5,6,7,8-hexahydro-2,7-dimethyl-4-(2-methylphenyl)-5-oxo-1,7-naphthyridine-3-carboxylic acid methyl ester.

4. The compound of claim 1 which is 1,4,5,6,7,8-hexahydro-2,7-dimethyl-5-oxo-4-[2-(trifluoromethyl)-phenyl]-1,7-naphthyridine-3-carboxylic acid methyl ester.

5. The compound of claim 1 which is 1,4,5,6,7,8-hexahydro-2,7-dimethyl-4-(3-nitrophenyl)-5-oxo-1,7-naphthyridine-3-carboxylic acid methyl ester.

6. The compound of claim 1 which is 1,4,5,6,7,8-hexahydro-2-methyl-4-(2-methylphenyl)-5-oxo-1,7-naphthyridine-3-carboxylic acid methyl ester.

7. The compound of claim 1 which is 4-(2-chlorophenyl)-1,4,5,6,7,8-hexahydro-2,7-dimethyl-5-oxo-1,7-naphthyridine-3-carboxylic acid methyl ester.

8. The compound of claim 1 which is 4-(2,6-dichlorophenyl)-1,4,5,6,7,8-hexahydro-2,7-dimethyl-5-oxo-1,7-naphthyridine-3-carboxylic acid methyl ester.

9. The compound of claim 1 which is 4-(2,5-dimethylphenyl)-1,4,5,6,7,8-hexahydro-2,7-dimethyl-5-oxo-1,7-naphthyridine-3-carboxylic acid methyl ester.

10. The compound of claim 1 which is 1,4,5,6,7,8-hexahydro-2-methyl-5-oxo-4-[2-(trifluoromethyl)phenyl]-1,7-naphthyridine-3-carboxylic acid methyl ester.

11. The compound of claim 1 which is 1,4,5,6,7,8-hexahydro-2-methyl-4-(3-nitrophenyl)-5-oxo-1,7-naphthyridine-3-carboxylic acid methyl ester.

12. The compound of claim 1 which is 1,4,5,6,7,8-hexahydro-2-methyl-5-oxo-4-[3-(trifluoromethyl)phenyl]-1,7-naphthyridine-3-carboxylic acid methyl ester.

13. The compound of claim 1 which is 4-(2-fluorophenyl)-1,4,5,6,7,8-hexahydro-2-methyl-5-oxo-1,7-naphthyridine-3-carboxylic acid methyl ester.

14. The compound of claim 1 which is 4-(3-cyanophenyl)-1,4,5,6,7,8-hexahydro-2,7-dimethyl-5-oxo-1,7-naphthyridine-3-carboxylic acid methyl ester.

15. The compound of claim 1 which is 4-(2,3-dimethylphenyl)-1,4,5,6,7,8-hexahydro-2,7-dimethyl-5-oxo-1,7-naphthyridine-3-carboxylic acid methyl ester.

16. The compound of claim 1 which is 4-[2-(n-butyl)-phenyl]-1,4,5,6,7,8-hexahydro-2-methyl-5-oxo-1,7-naphthyridine-3-carboxylic acid methyl ester.

17. The compound of claim 1 which is 4-(2,3-dimethylphenyl)-1,4,5,6,7,8-hexahydro-2-methyl-5-oxo-1,7-naphthyridine-3-carboxylic acid methyl ester.

18. A compound of the formula:

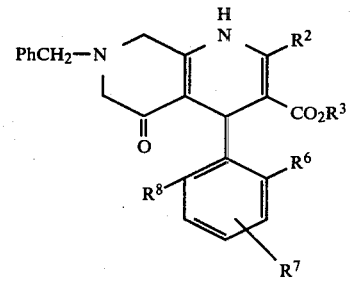

in which
PhCH₂ is benzyl;
R² is alkyl of 1 to 6 carbon atoms;
R³ is alkyl of 1 to 6 carbon atoms, alkoxyalkyl in which each alkyl moiety has 1 to 6 carbon atoms, —CH₂CF₃, —CH₂CH₂CF₃ or

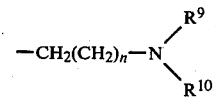

where R⁹ is hydrogen or alkyl of 1 to 6 carbon atoms and R¹⁰ is alkyl of 1 to 6 carbon atoms or arylalkyl of 7 to 10 carbon atoms and R⁹ and R¹⁰ taken with the nitrogen atom to which they are attached form a pyrrolidinyl, imidazolidinyl, piperidyl, piperazinyl, 4-alkylpiperazinyl in which the alkyl group contains from 1 to 6 carbon atoms or morpholinyl heterocycle, and n is one of the integers 0, 1 or 2;
R⁶ and R⁸ are, independently, hydrogen, alkyl of 1 to 6 carbon atoms, halo, trifluoromethyl, alkoxy of 1 to 6 carbon atoms, alkylthio of 1 to 6 carbon atoms, cyano or nitro;

$R^7$ is hydrogen, alkyl of 1 to 6 carbon atoms, halo, trifluoromethyl, cyano or nitro; and $R^6$ and $R^7$ when in ortho position to each other and taken together are butadienylene, tetramethylene or trimethylene;

or a pharmaceutically acceptable salt thereof.

19. The compound of claim 18 which is 1,4,5,6,7,8-hexahydro-2-methyl-4-(2-methylphenyl)-5-oxo-7-(phenylmethyl)-1,7-naphthyridine-3-carboxylic acid methyl ester.

20. The compound of claim 18 which is 1,4,5,6,7,8-hexahydro-2-methyl-5-oxo-7-(phenylmethyl)-4-[2-(trifluoromethyl)-phenyl]-1,7-naphthyridine-3-carboxylic acid methyl ester.

21. The compound of claim 18 which is 1,4,5,6,7,8-hexahydro-2-methyl-4-(3-nitrophenyl)-5-oxo-7-(phenylmethyl)-1,7-naphthyridine-3-carboxylic acid methyl ester.

22. The compound of claim 18 which is 4-[2-(n-butyl)-phenyl]-1,4,5,6,7,8-hexahydro-2-methyl-5-oxo-7-(phenylmethyl)-1,7-naphthyridine-3-carboxylic acid methyl ester.

23. The compound of claim 18 which is 4-(2,3-dimethylphenyl)-1,4,5,6,7,8-hexahydro-2-methyl-5-oxo-7-(phenylmethyl)-1,7-naphthyridine-3-carboxylic acid methyl ester.

24. The compound of claim 18 which is 1,4,5,6,7,8-hexahydro-2-methyl-5-oxo-7-phenylmethyl-4-[2-(trifluoromethyl)phenyl]-1,7-naphthyridine-3-carboxylic acid, 2-(N-benzyl-N-methyl)aminoethyl ester.

* * * * *